United States Patent
Jakus

(10) Patent No.: US 8,323,274 B2
(45) Date of Patent: Dec. 4, 2012

(54) ABLATION CATHETER ARRANGEMENT AND COOLING CONTROL

(75) Inventor: Laszlo Jakus, Pilisszanto (HU)

(73) Assignee: Biotronik CRM Patent AG, Baar (CH)

( * ) Notice: Subject to any disclaimer, the term of this patent is extended or adjusted under 35 U.S.C. 154(b) by 876 days.

(21) Appl. No.: 12/355,001

(22) Filed: Jan. 16, 2009

(65) Prior Publication Data

US 2009/0187186 A1 Jul. 23, 2009

(30) Foreign Application Priority Data

Jan. 17, 2008 (DE) .......... 10 2008 004 972

(51) Int. Cl.
*A61B 18/18* (2006.01)
*A61F 7/00* (2006.01)
*A61F 7/12* (2006.01)

(52) U.S. Cl. .......... 606/22; 607/96

(58) Field of Classification Search ........ 606/40, 606/41, 22–26, 102; 607/96
See application file for complete search history.

(56) References Cited

U.S. PATENT DOCUMENTS

| | | |
|---|---|---|
| 5,893,884 A | 4/1999 | Tu |
| 6,053,912 A | 4/2000 | Panescu et al. |
| 2003/0004506 A1 | 1/2003 | Messing |
| 2005/0065584 A1* | 3/2005 | Schiff et al. ......... 607/105 |
| 2005/0090814 A1 | 4/2005 | Lalonde |
| 2005/0171582 A1 | 8/2005 | Matlock |
| 2008/0091193 A1* | 4/2008 | Kauphusman et al. ...... 606/41 |

OTHER PUBLICATIONS

European Search Report, dated May 27, 2009.
Da Costa et al. "Catheter selection for ablation of the cavotricuspid isthmus for treatment of typical atrial flutter" Journal of Interventional Cardiac Electrophysiology.

* cited by examiner

*Primary Examiner* — Nicholas Lucchesi
*Assistant Examiner* — Rebecca E Eisenberg
(74) *Attorney, Agent, or Firm* — ARC IP Law, PC; Joseph J. Mayo

(57) ABSTRACT

An apparatus for cooling ablation catheters via a coolant pump and liquid cooling medium controlled by a controller based on a characteristic state for an activity of a catheter and in addition a system that uses the apparatus for ablation of tissue in a human or animal body. The system includes an elongated ablation catheter, an ablation generator electrically connected to the catheter to generate a high-frequency energy pulse or a high-frequency energy field, the coolant pump connected to the catheter and the controller and a control line connected to the pump. The control line comprises an electric circuit designed to detect a high-frequency pulse or a high-frequency field.

17 Claims, 2 Drawing Sheets

ABLATION CATHETER ARRANGEMENT AND COOLING CONTROL

This application takes priority from German Patent Application DE 10 2008 004 972.7, filed 17 Jan. 2008, the specification of which is hereby incorporated herein by reference.

BACKGROUND OF THE INVENTION

1. Field of the Invention

The invention relates to an ablation catheter arrangement for high-frequency ablation of tissue, in particular for targeted creation of linear and/or spot lesions in coronary tissue.

2. Description of the Related Art

Heart disease is widespread. The most common diseases affecting the myocardium but not the coronary vessels involve the conduction of stimuli. With normal stimulus conduction, these electric stimuli are formed by the sinus node, which is situated in or on the right auricle of the heart, and propagate over the entire myocardium by way of the AV node (atrioventricular node), the His bundle, the Tawara branch and the Purkinje fibers, to thereby induce contraction of the heart from the apex of the heart and proceeding to the atria by way of the myocardium of the two ventricles. This results in a circulation path.

Interference-free stimulus conduction then leads to the physiologically trouble-free ejection of blood into the pulmonary artery and aorta. The structure of the coronary tissue, which behaves like a muscle that can be stimulated equally at all points and in all directions, is noteworthy. In a healthy heart, after successful activation of the ventricular musculature, stimulus conduction is blocked by equal polarization of all muscular cells, so that no potential difference is capable of enabling electric stimulus conduction. This condition is known as the refractory time because all the muscle cells are refractory and cannot be stimulated. This condition dissipates on its own after a short period of time to allow the next stimulus and thus the next heartbeat.

If there is an anatomical or functional obstacle—for example, in a bundle of branching Purkinje fibers, then a dangerous intermediate stage may occur before the conduction is completely blocked at this point: a unidirectional block. The damaged area here retards the passage of a stimulus until at some point it becomes refractory with respect to the next stimulus, i.e., this area is difficult or impossible to stimulate. However, this stimulation can pass through the damaged area in the opposite direction because it reaches this damaged area at a later point in time, at which it may no longer be refractory. The transit time delay occurs due to the "detour" by which the stimulus must travel.

If the remaining refractory path behind this stimulus, which is now running in the opposite direction (technical term: retrograde conduction), is shorter than the circulation path, the stimulus does not die out within the circulation path and can run through it continuously. In this case we speak of a circulating stimulus.

The risk here is of reentry of the stimulus wave into the surrounding tissue when the latter is no longer refractory. A stimulus that would otherwise be self-sustaining, so to speak, may develop. This is the cause of serious tachycardiac arrhythmias associated with the risk of fibrillation.

In addition to medication therapies, electrophysiological therapy has become successful here. Certain spots on the myocardium are heated by high frequency in a targeted manner and are thereby ablated to prevent the electrical conduction. Ablated tissue is no longer conductive.

Ablation catheter arrangements are used for ablation therapy.

As indicated by the name, these include an ablation catheter and an ablation generator plus a coolant pump.

The ablation catheter is an elongated catheter which is guided through a blood vessel to the treatment site. It includes an electrically insulating tubular sheath and electrically conductive feeder lines and coolant flow paths running inside the sheathing. On the distal end there are electrode poles suitable for delivering high-frequency energy pulses. The electrode poles are pointed or flat and are electrically connected to the feeder lines. In addition, an ablation catheter may contain control means with which the distal catheter section can be brought into a linear or circular form, for example. Linear lesions or circular lesions can thus be created around the mouth of the pulmonary veins, for example.

At the output end, the ablation generator generates a high-frequency energy pulse signal or a high-frequency energy field, which is sent to the feeder lines of the ablation catheter and is sent from there to the electrode poles for delivery to the coronary tissue. The generator is controlled by an operator. A device for cooling ablation catheters which supplies a liquid cooling medium (usually a physiological saline solution) in the at least one coolant path of the ablation catheter on demand by the operator, whereby the coolant leads through the coolant path up to the electrode poles on the distal section or on the distal end. The catheter and the ablation site are therefore both cooled by circulating the coolant through the catheter either through another coolant path and/or by guiding the coolant to the ablation site through openings in the distal section. The cooling device also has a controller which controls the pump, so that it generates at least one lower flow rate and one elevated flow rate. In this way, the cooling device ensures a uniform and constant flow of coolant through the catheter to the electrode poles at a low flow rate. If the operator prompts the delivery of a high-frequency signal, increased delivery of coolant is required. The operator makes this demand by creating an increased flow rate in the cooling device by means of a foot pedal simultaneously with the control of the ablation generator. This produces an even greater cooling.

One disadvantage of this manual control is that the operator must operate two different systems. This operation alone requires so much concentration and training that there may easily be mistakes in guidance of the catheter. Even if the control of the cooling device is performed by an assistant, coordination of the operation of the catheter, the ablation generator and the pump requires a great deal of concentration and coordination.

Known further developments include ablation arrangements constructed so that the generator and a specific cooling device which is compatible with the generator cooperate. These arrangements are always coordinated with one another in such a way that replacement of the generator involves replacement of the cooling device at the same time. On delivery of a high-frequency pulse, the generator switches the flow rate of the pump to an increased coolant flow. The pulse and the coolant are fed into the catheter via a proprietary interface between the catheter on the one hand and the generator and the pump on the other hand. It is thus a disadvantage that the operator is limited to precisely such a pair of devices, i.e., the ablation generator and the pump.

An individual adjustment, which is sometimes also based on the indication and the type of catheter associated with it or the required energy output is thus impossible. It may thus be necessary during a treatment to change to another ablation generator while retaining the cooling device and the constant cooling with the low coolant flow and the increased coolant flow, e.g., because a higher ablation energy is required, an incompatible ablation catheter must be used, or because the ablation generator is defective. With the ablation arrangements known in the past, the user loses the automatic coupling of the cooling device to the ablation generator because the pump cooperates only with the compatible generator. Cooling of the catheter must thus be interrupted or, as described above, controlled manually. The interruption in cooling may be very painful for the patient due to the catheter heating up again and may also lead to a loss of volume of the catheter tubing because the volume of the cooling liquid is maintained. Under certain conditions, the loss of catheter cooling may also be a risk to the patient. Manual control has the disadvantages described above.

BRIEF SUMMARY OF THE INVENTION

It is therefore desirable to eliminate the aforementioned disadvantages and provide a coolant pump for the purposes of ablation of coronary tissue, which can be controlled and used independently of the ablation generator and which ensures cooling during all the operating modes described here without the operator having to perform the control of the cooling himself. In addition, it is desirable to create an arrangement that ensures cooling during ablation and is performed without intervention or control by the operator.

The first object is achieved in that the controller has an interface that is designed to detect a characteristic state for the activity of the catheter at the input end and to output to the controller at the output end a request signal representing this detection. Due to this autonomous cooling device, the work of the operator is simplified, so that he can concentrate on the essential process steps in ablation. Due to the prevailing operating mode of the catheter, the controller of the cooling device detects the demand for cooling. Injury to the patient or unintentional pain due to faulty operation of the pump or incorrect coolant flow (too low) are therefore ruled out.

The controller of the cooling device advantageously sends a control signal to the coolant pump to increase the flow rate when the request signal of the interface is such that it represents exceeding the threshold of the state detected at the input end. This threshold value especially preferably relates to the temperature at the ablation site and is preferably between 37.5° C. and 40° C. Additionally or alternatively, the threshold value relates to the voltage coming from the temperature sensor, whereby the threshold value may be in a voltage range between a few mV (preferably 10 mV) and 5 V, depending on the technical embodiment of the temperature sensor. Additionally or alternatively, the threshold value may relate to an ablation frequency range, such that the threshold value is in a frequency range between 450 kHz and 550 kHz. Likewise, in addition and as an alternative to the aforementioned threshold values, the high-frequency current on the catheter feeder line can be detected, such that the threshold value is between a few milliamperes and 2 A. Likewise, in addition or as an alternative to the aforementioned threshold values, the impedance in the treatment region can be detected, such that the threshold value is between 120 and 250 ohm.

The use of the coolant device is therefore further improved and made more reliable in that the request for a change in coolant flow is implemented on the basis of objectively measurable values which are independent of the operator.

The controller also preferably sends a control signal to the coolant pump which depends on the request signal from the interface, so that the coolant pump generates a flow rate corresponding to the state detected at the input end. In this way, the system is further improved by generating a flow rate, which is determined by its direct reference to the state on the ablation catheter. In other words, the controller adjusts the pump so as to result in a continuous and continuously adjustable coolant flow that is a direct function of the detected state (temperature, electric current, frequency and/or impedance). The cooling device can thus react adequately and appropriately to extremely minor changes in temperature, electric current, energy and/or impedance. This leads to a reliable and safe treatment with the most uniform possible conditions.

The controller preferably controls the coolant pump in such a way that it creates the lower flow rate without a request signal from the interface. In other words, a continuous coolant flow is achieved, thereby ensuring secondary cooling after successful ablation and contributing further toward pain relief or reduced injuries. It also prevents blood from penetrating into the coolant pathway and clogging it. Furthermore, the operator is enabled to change the ablation generator without having to replace the pump. Continuous cooling is thus ensured.

In the simplest case, the interface having a cable with an adapter for galvanically direct or indirect detection on its end facing away from the controller. This adapter may assume various forms. For example, the adapter may be embodied in the form of eyes, tubes or prongs. This shape entails the advantage that the adapter can easily be attached universally to all conventional catheters or their feeder lines. To do so, the eye or the tube is pushed over the catheter shaft, so that an electric field, for example, can be measured when an ablation is being performed. According to one alternative, the adapter is designed as a plug, so that it can be connected directly to the generator or to the catheter, for example. On the catheter, this is possible on the connecting line for the temperature measurement, for example, where the temperature sensors are connected electrically to the distal end of the ablation catheter. The coolant flow can be adjusted as a function of the measured temperature. In addition, it is possible to deduce the temperature at the treatment site based on the measured impedance because the impedance increases when the temperature is above the physiologically normal temperature.

In one embodiment, the aforementioned cable has an electric circuit which converts the state that is detected at the input end and is characteristic of the activity of the catheter into a request signal at the output end. This may be an A/D converter. The circuit especially preferably also includes means to ensure adequate seating of the adapter for error-free detection of the state that is characteristic of the activity of the catheter; these means preferably include a Hall sensor on the adapter. In addition, the means of the circuit may include an acoustic or visual signal generator, which is especially preferably a light-emitting diode. This indicates whether the adapter is adequately seated on the catheter and whether error-free detection is possible. This produces a reliable measurement to further rule out any injury of the patient during the treatment.

In another embodiment, the interface has an adapter on its end facing away from the controller for non-contact near-field or far-field detection, said adapter preferably being designed as high-frequency antenna. This further increases the ease of operation for the operator because the interfering cable may be omitted.

The second task is achieved with an arrangement for ablation of tissue in a human or animal body. This arrangement comprises, in addition to the cooling device described above, an elongated ablation catheter having a connection piece and a catheter tubing which is guided over (i.e., on/via/through or anywhere near) a vessel to the treatment site. In addition, the arrangement includes an ablation generator which is electrically connected to the catheter and generates a high-frequency energy pulse or a high-frequency energy field at the output end and sends it via a connecting line to the ablation catheter.

The coolant pump of the cooling device is designed to pump a liquid coolant medium via a connecting line into at least one cooling path of the ablation catheter. The invention is also characterized in that the interface of the cooling device is galvanically connected to the generator at the input end, either directly and/or indirectly and/or via near-field/far-field detection, to detect the state that is characteristic of the activity of the catheter. The operator is thus free to make his choice of instruments and catheters and has several options for performing the ablation in an optimized manner because the operator is able to replace the generator independently of the catheter, while cooling is still ensured. This arrangement is thus modular, so that the universally usable pump can be used with any type of generator and catheter.

The interface of the cooling device preferably has an adapter which is connected to the generator, to the electric connection line of the generator or to the connection piece of the ablation catheter.

BRIEF DESCRIPTION OF THE DRAWINGS

The invention will now be explained on the basis of two exemplary embodiments, in which.

DETAILED DESCRIPTION OF THE INVENTION

Figure 1:
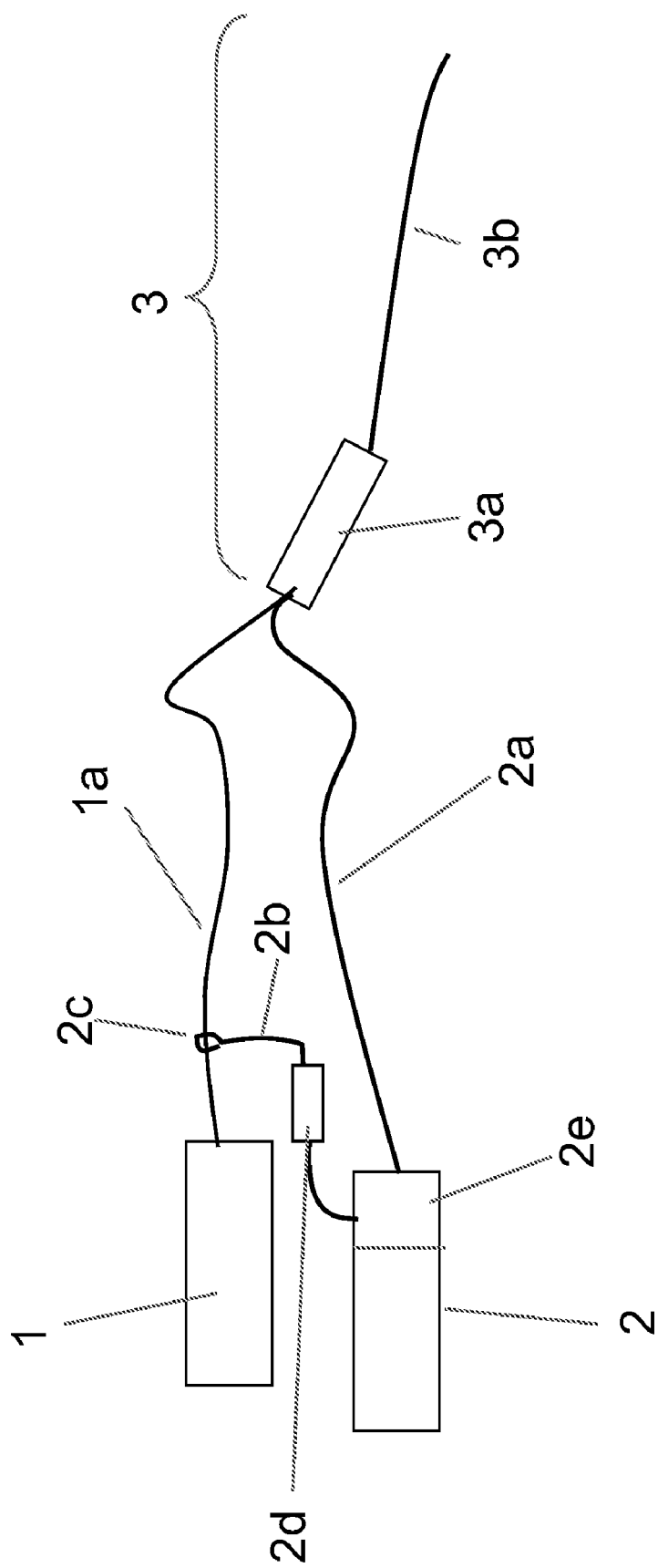
FIG. 1 shows a first exemplary embodiment by pickup of a high-frequency signal on the electric connecting line.

FIG. 1 shows an ablation arrangement comprising an ablation generator 1, a coolant pump 2 and a catheter 3, shown here with a connection piece 3a situated on the proximal end, with the help of which the generator 1 and the pump 2 can be connected. The connection piece 3a establishes the electric connection between the generator 1 and the electric feeder lines (not shown) and a tight connection between the coolant pump 2 and the coolant channel (not shown). The elongated catheter tubing is indicated with the notation 3b. The electrode poles for transmitting the high-frequency energy to the tissue and the control device are also not shown here.

The generator is connected to an electric connecting line 1a, while the pump is connected to a hollow connecting line 2a carrying coolant via the connection piece 3a. Physiological saline solution is used as the coolant.

In addition, the pump 2 comprises a control line 2b, which is electrically connected to the electric connection line 1a. The control line may also be connected according to this invention to the connection piece 3a or to the electric feeder line of the catheter 3. The control line 2b serves to detect a high-frequency pulse or a high-frequency field delivered by generator 1 via the connecting line 1a to the catheter 3. The electric connection between the control line 2b and the connecting line 1a is established according to this invention with an adapter 2c—conventional commercial and/or standardized plugs, electric clamping adapters such as a clamping prong or other suitable means may also be used. However, eyes or tube segments that can easily be pushed over the catheter are also possible.

On the other hand, the control line 2b is connected at the input end to another electric controller 2e, which controls the pump.

The control line 2b or the adapter 2c contains an electronic circuit unit 2d which detects a high-frequency electric pulse or a field applied to the connecting line 1a.

The electric circuit unit 2d detects the field strength applied to the connecting line 1a. If the measured field strength in a defined frequency band exceeds or falls short of a threshold value, then the electronic system of the prong adapter switches a trigger level. This trigger level is used to trigger the controller 2e of the pump 2 which switches between two flow rates. Thus if a high field strength is applied to the connecting line 1a and thus to the adapter 2c, then the output signal of the circuit unit 2d is such that the controller 2e switches to the higher flow rate. This is the case when an ablation process is started. When the ablation process is ended, the field strength falls below the threshold value and the signal of the circuit unit 2d at the output end is such that the controller 2e switches the pump to a lower flow rate.

The circuit unit 2d may advantageously contain a delay element which sends a delayed output signal to the controller 2e only when the value drops below a threshold value in order to achieve complete cooling.

This ensures that the coolant pump will allow a minimal continuous flow rate independently even if the generator 1 is turned off or is being replaced. The cooling and the function of the catheter are thus still possible.

Figure 2:
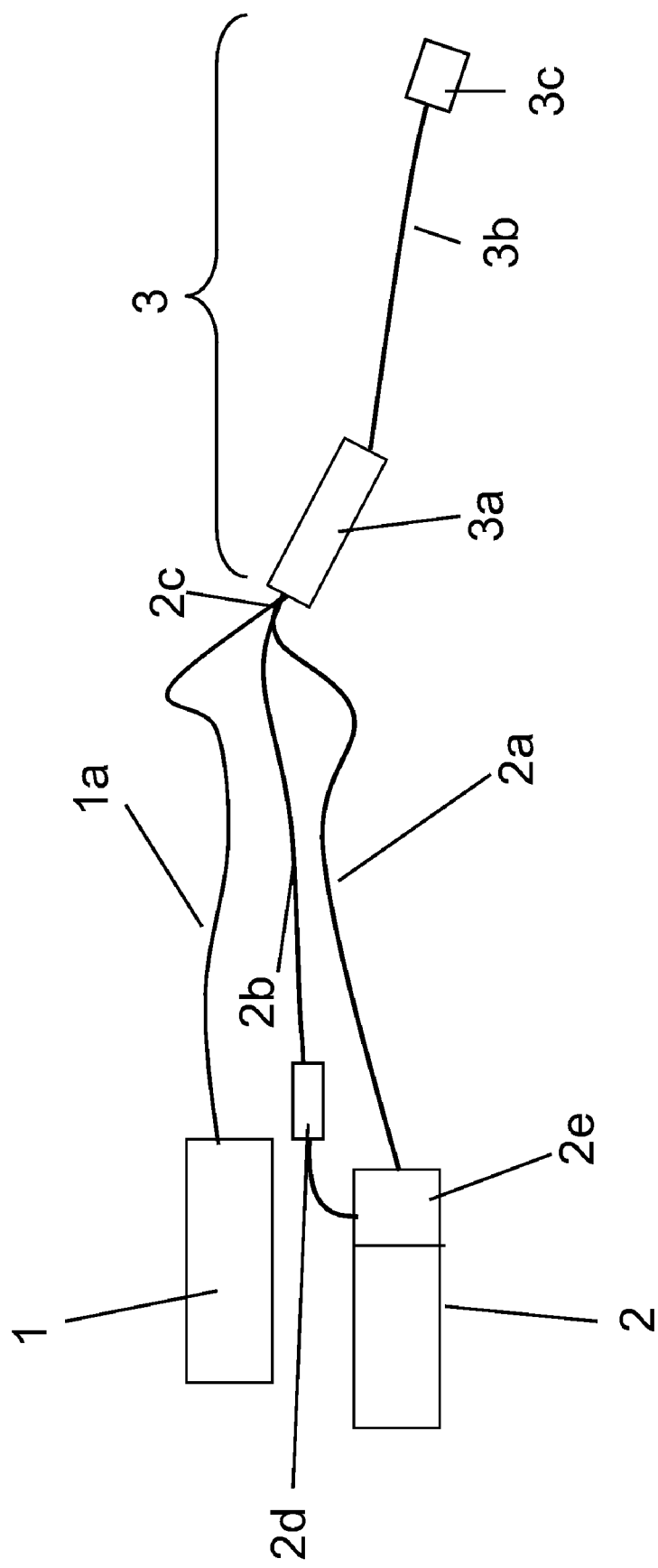
FIG. 2 shows a second exemplary embodiment by measurement of a sensor voltage of a temperature sensor at the catheter tip.

FIG. 2 shows an ablation arrangement that includes an ablation generator 1, a coolant pump 2, a catheter 3, shown here with a connection piece 3a situated on the proximal end, with the help of which the generator 1 and the pump 2 can be connected. The connection piece 3a establishes the electric connection between the generator 1 and the electric feeder lines (not shown here) and a tight connection between the coolant pump 2 and the coolant channel (not shown here). The elongated catheter tubing is indicated with 3b as the nomenclature. The electrode poles for transmitting the high-frequency energy to the tissue and the control device are also not shown.

The generator is connected to an electric connecting line 1a, while the pump is connected to a hollow connecting line 2a carrying the coolant via the connection piece 3a. Physiological saline solution is used as the coolant.

In addition, the pump 2 includes a control line 2b, which is connected to the connection piece 3a or the electric feeder line of the catheter 3. The control line 2b serves to detect the signal measured by the temperature sensor 3c at the tip of the catheter and delivered through the catheter 3 and the electric connecting line 1a to the generator 1. The electric connection between the control line 2b and the connecting line 1a is established according to the invention with an adapter 2c (commercial and/or standardized plugs are suitable).

On the other hand, the control line 2b is connected at the input end to another electric controller 2e which controls the pump.

The control line 2b or the adapter 2c contains an electronic circuit unit 2d that detects a temperature signal measured on the temperature sensor 3c and delivered to the generator 1 via the catheter 3 and the connecting line 1a.

In this process, the electric circuit unit 2d measures the voltage of the temperature signal applied to the connecting line 1a. If the measured voltage exceeds or falls below a defined voltage threshold value, the electronic circuit unit 2d switches a trigger level. This trigger level is used to trigger the controller 2e of the pump 2, which switches between two flow rates. If a high voltage is applied to the connecting line 1a and thus to the adapter 2c, the output signal of the circuit unit 2d is such that the controller 2e switches to the higher flow rate. This is the case when an ablation process is started and therefore the temperature in the catheter tip is increased. When the ablation process is ended, the voltage coming from the temperature sensor drops below the threshold value and the signal of the circuit unit 2d on the output end is such that the controller 2e switches the pump to a low flow rate.

This ensures that the coolant pump 2 will allow a minimal continuous flow rate independently, even when the generator 1 is turned off or is being replaced. The cooling and the function of the catheter 3 are thus still possible.

What is claimed is:

1. A device for cooling ablation catheters, comprising:
   a coolant pump (2) configured to supply a liquid cooling medium on demand with a low flow rate and an elevated flow rate in a connecting line (2a);
   a controller (2e) which controls the coolant pump so that the coolant pump supplies either the low flow rate or the elevated flow rate of the liquid cooling medium; and,
   said controller further comprising an interface (2b), which is configured
      to detect a characteristic state for an activity of a catheter at an input end of said interface (2b);
      to output a request signal that represents the characteristic state to the controller at an output end of said interface (2b);
   wherein the controller (2e) sends a control signal to switch from said low flow rate to said elevate flow rate to the coolant pump (2) when the request signal from the interface (2b) is such that the request signal represents a value that exceeds a threshold value of the characteristic state detected at the input end of said interface (2b).

2. The device according to claim 1, wherein the controller (2e) sends a control signal to switch from said elevated flow rate to said low flow rate to the coolant pump (2) when the request signal from the interface (2b) is such that the request signal represents a value that does not exceed a threshold value of the characteristic state detected at the input end and wherein said control signal is sent after a time delay.

3. The device according to claim 2 wherein the threshold value is in a temperature range between 37.5° C. and 40° C. and/or in a frequency range between 450 kHz and 550 kHz and/or in a range of high-frequency current between a mA and 2 A or a voltage range between 1 mV and 5 V and/or an impedance range between 120 ohm and 250 ohm.

4. The device according to claim 1, wherein the controller (2e) is configured to control the coolant pump (2) such that the coolant pump supplies the lower flow rate without the request signal from the interface (2e).

5. The device according to claim 1, wherein the interface (2b) is a cable, which has on its end that faces away from the controller (2e), an adapter (2c) for direct or indirect detection of the characteristic state, wherein the adapter is configured in the form of an eye, tube or prongs or as a plug.

6. The device according to claim 5, wherein the cable has an electric circuit (2d), which converts the characteristic state that is detected at the input end which is characteristic of the activity of the catheter into the request signal at the output end.

7. The device according to claim 1, wherein the interface (2b) is a cable, which has on its end that faces away from the controller (2e), an adapter (2c) for galvanically direct or indirect detection of the characteristic state, wherein the adapter is configured in the form of an eye, tube or prongs or as a plug.

8. The device according to claim 7, further comprising an electrical circuit (2d) is configured to securely seat an adapter (2c) for error-free detection of the characteristic state which is characteristic of the activity of the catheter, and wherein the adapter (2c) further comprises a Hall sensor.

9. The device according to claim 8, wherein the electrical circuit (2d) also comprises an acoustic or visual signal generator, or a light-emitting diode, which indicates that the adapter is securely seated and that error-free detection is thus possible.

10. The device according to claim 1, wherein the interface (2b) comprises an adapter (2c) for non-contact near-field or far-field detection of the characteristic state on an end facing away from the controller, wherein said adapter is configured as a high-frequency antenna.

11. The device according to claim 1 further comprising:
    wherein said catheter is an elongated ablation catheter (3) comprising a connection piece (3a) and a catheter tubing (3b) which is guided over a vessel to a treatment site;
    an ablation generator (1) which is electrically connected to the elongated ablation catheter, wherein the ablation generator is configured to generate a high-frequency energy pulse or a high-frequency energy field at an output end that is sent to the elongated ablation catheter over an electrical connecting line (1a).

12. The system of claim 11 wherein the interface is connected to the ablation generator and/or elongated ablation catheter via a direct connection.

13. The system of claim 11 wherein the interface is connected to the ablation generator and/or elongated ablation catheter via a galvanically direct connection.

14. The system of claim 11 wherein the interface is connected to the ablation generator and/or elongated ablation catheter via an indirect connection.

15. The system of claim 11 wherein the interface is connected to the ablation generator and/or elongated ablation catheter via an indirect connection comprising a near field connection.

16. The system of claim 11 wherein the interface is connected to the ablation generator and/or elongated ablation catheter via an indirect connection comprising a far field connection.

17. The system according to claim 11, wherein the interface (2b) has an adapter (2c) which is connected to
    the ablation generator (1),
    the electric connecting line (1a) of the ablation generator (1), or
    the connection piece (3a) of the elongated ablation catheter (3).

* * * * *